Figure 1:
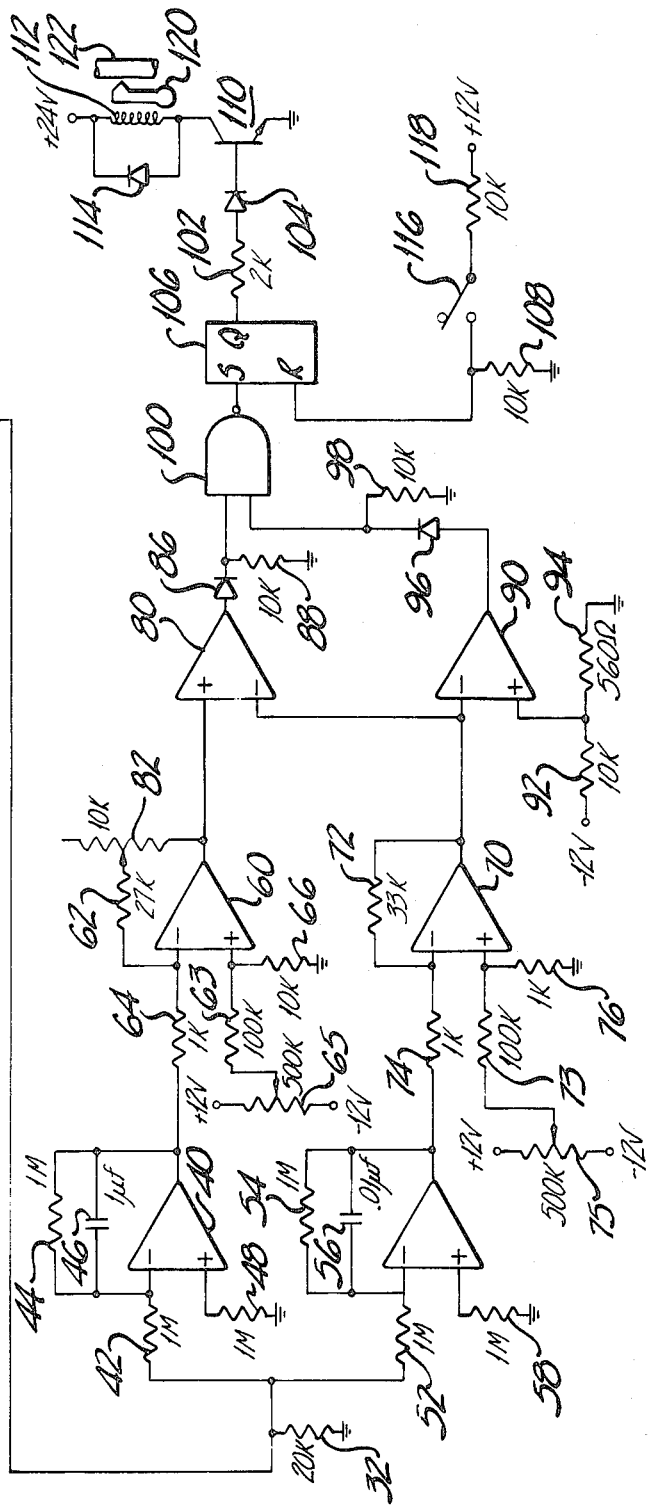

United States Patent [19]

Lindemann

[11] Patent Number: 4,487,601
[45] Date of Patent: Dec. 11, 1984

[54] BUBBLE DETECTOR CIRCUIT WITH VARIABLE REFERENCE LEVEL

[75] Inventor: William T. Lindemann, Yardley, Pa.

[73] Assignee: Extracorporeal Medical Specialties, Inc., King of Prussia, Pa.

[21] Appl. No.: 505,652

[22] Filed: Jun. 20, 1983

[51] Int. Cl.³ .............................................. A61M 5/14
[52] U.S. Cl. ...................................... 604/122; 604/67; 128/DIG. 13
[58] Field of Search ............... 604/122, 31, 50, 65–67, 604/244; 128/DIG. 13; 73/19; 340/603

[56] References Cited

U.S. PATENT DOCUMENTS

| | | | |
|---|---|---|---|
| 2,835,252 | 5/1958 | Mauchel | 604/122 |
| 3,935,876 | 2/1976 | Massie et al. | 604/122 X |
| 4,014,206 | 3/1977 | Taylor | 604/122 X |
| 4,137,913 | 2/1979 | Georgi | 604/67 |
| 4,280,495 | 7/1981 | Lampert | 604/67 X |
| 4,344,429 | 8/1982 | Gupton et al. | 128/DIG. 13 |
| 4,354,502 | 10/1982 | Lolloy et al. | 604/122 |
| 4,367,736 | 1/1983 | Gupton | 128/DIG. 13 |
| 4,383,252 | 5/1983 | Purcell et al. | 604/31 X |

*Primary Examiner*—Edward M. Coven
*Attorney, Agent, or Firm*—Mark A. Hofer

[57] ABSTRACT

A bubble detector system is provided which dynamically responds to changes in energy transmission efficiency. The output of a detector is coupled to a dynamic reference level circuit, which develops a reference level that changes slowly in a time-varying manner with changes in the energy level received by the detector. The output of the detector is also coupled to a bubble detector circuit which produces a detection signal that changes rapidly when gas is present between an energy source and the detector. The detection and reference levels are compared to detect the presence of gas in the flow of fluid between the energy source and the detector.

8 Claims, 4 Drawing Figures

BUBBLE DETECTOR CIRCUIT WITH VARIABLE REFERENCE LEVEL

The present invention relates to systems for detecting the pressure of gas bubbles in fluids and, in particular, to improved circuitry for bubble detectors which provides a variable detection reference level.

In hemodialysis, blood is drawn from a patient whose kidneys no longer properly perform their function of blood purification. The hemodialysis system pumps the patient's blood through a dialyzer, where impurities in the blood are removed through diffusion through a membrane. The purified blood is then returned to the patient.

Hemodialysis systems conventionally employ apparatus such as blood drip chambers which are filled with blood to predetermined levels during the hemodialysis procedure. Means such as blood level detectors are then generally used to monitor the blood level within the drip chambers. Similar apparatus is used to monitor the blood as it is returned to the patient to ensure that the blood does not contain air bubbles. The return of blood to the patient which is contaminated with sizeable air bubbles can be harmful or even fatal to the patient under certain circumstances.

Blood level and bubble detectors generally operate in the same manner. An energy source, such as a light source or a source of ultrasound, is positioned on one side of the drip chamber or blood tubing, and a detector of such energy is placed on the opposite side of the drip chamber or tubing. When blood is present between the energy source and the detector, a certain amount of energy is continuously received by the detector. But when the blood level drops in the drip chamber, or bubbles are present in the blood, the amount of energy received by the detector changes. The detector output signal changes, which signal change can be used to trigger an alarm which may halt the hemodialysis procedure.

The amount of energy received during normal operation of the system is a function of the efficiency of energy coupling through the drip chamber or blood tubing and blood flow which is located between the energy source and the detector. In the case of ultrasound, for instance, it is desirable to snugly fit the chamber or tubing between the ultrasonic transmitter and detector to provide efficient energy transmission. The presence of air between the two will cause scattering of the ultrasonic energy, thereby reducing the amount of energy received by the detector. The existence of such a condition can lead to excessive false alarms and interruption of the hemodialysis treatment if means are not provided to overcome the problem.

In accordance with the principles of the present invention, detection circuitry for a bubble detector is provided which dynamically responds to changes in energy transmission efficiency. The output of the detector is coupled to a dynamic reference level circuit, which develops a reference level that changes slowly in a timevarying manner with changes in the energy level received by the detector. The output of the detector is also coupled to a bubble detector circuit which produces a detection signal that changes rapidly when gas is present between the energy source and the detector. The detection and reference levels are compared to detect the presence of gas in the blood flow. Under normal operating conditions, a substantially fixed differential exists between the levels of the two signals, independent of energy coupling efficiency between the source and the detector.

Figure 2A:
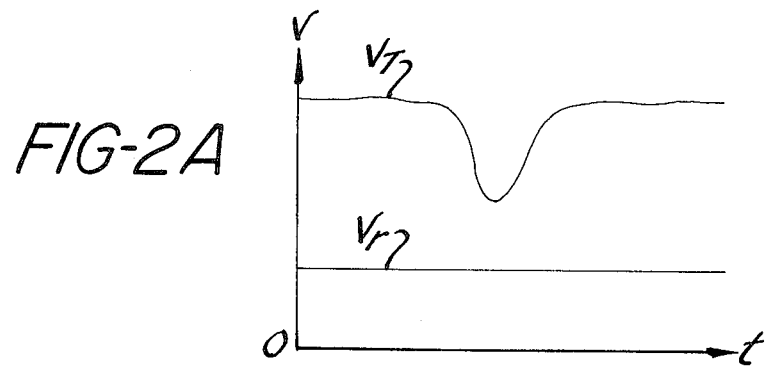
Figure 2B:
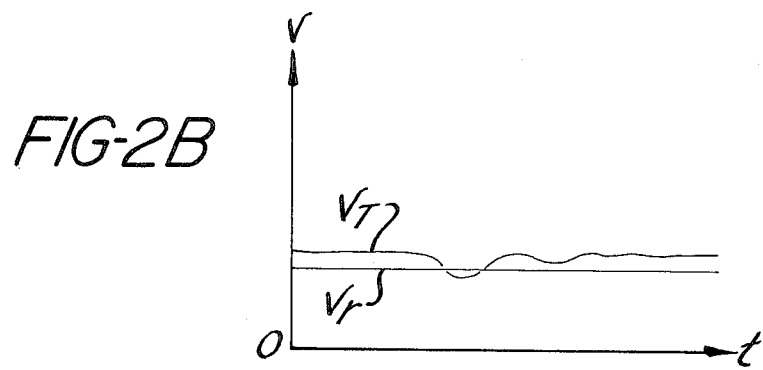
Figure 2C:
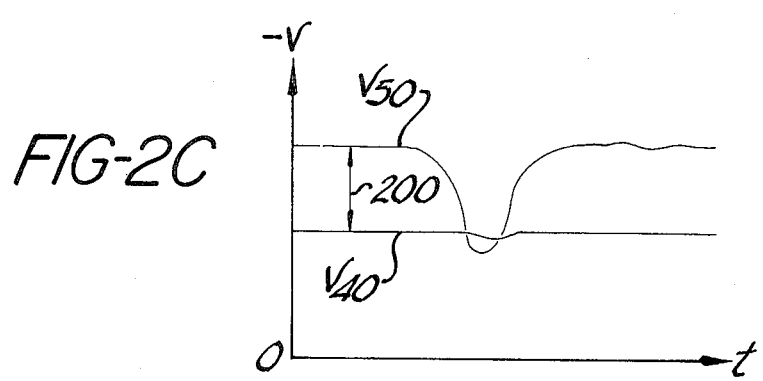

In the drawings:

FIG. 1 illustrates, partially in block diagram form and partially in schematic diagram form, a bubble detector constructed in accordance with the principles of the present invention; and FIGS. 2A, 2B and 2C illustrate waveforms useful for explaining the operation of the bubble detector of FIG. 1.

Referring to FIG. 1, a bubble detector circuit constructed in accordance with the principles of the present invention is shown. An oscillator 10 provides oscillatory signals to drive an ultrasonic transducer. The oscillator may have a frequency of 300 KHz, for instance. The oscillatory signals are amplified by an amplifier 12 and are coupled by a coupling capacitor 14 to a transducer 22. The transducer 22 is thereby activated to transmit ultrasonic waves across the opening of an ultrasonic transceiver 20, where the waves are received by a second ultrasonic transducer 24. A section of blood tubing or a blood drip chamber is normally interposed between the transducers 22 and 24. When the tubing or drip chamber contains blood which is not contaminated with air bubbles, the ultrasonic waves will be conveyed by the blood from transducer 22 to transducer 24 with little attenuation. Transducer 24 will then convert the received ultrasonic energy into relatively strong electrical signals. But when bubbles are present in the blood between the transducers, or the blood level is below the tubing section between the transducers, the ultrasonic waves will be scattered and attenuated by the air in the ultrasonic wave path. Transducer 24 will then receive relatively less ultrasonic energy, which will be converted into relatively weaker electrical signals.

The signals produced by transducer 24 are coupled by way of a coupling capacitor 16 to the input of an amplifier 18, where they are amplified to relatively higher oscillatory signal levels. The amplified signals are applied to a half-wave rectifier 30, which filters the signal to pass only the negative excursions of the oscillatory signal and provides further amplification. The amplified and rectified signals are dropped across a load resistor 32 and applied to the inputs of integrators 40 and 50.

Integrator 40 includes an input resistor 42 coupled to its inverting input, a feedback resistor 44 coupled between its output and its inverting input, and a resistor 48 coupled between its noninverting input and ground. Integrator 50 includes similar resistors 52, 54 and 58. Integrator 40 also includes a feedback capacitor 46 and integrator 50 includes a feedback capacitor 56, the two capacitors having distinctly different values. With the integrator component values shown in FIG. 1, the time constants of the two integrators will differ by two orders of magnitude since the capacitor values differ by this amount and the other component values are the same. For the embodiment of FIG. 1, integrator 40 has a one second time constant, and integrator 50 has a ten millisecond time constant.

The output of integrator 40 is coupled to the inverting input of an amplifier 60 by a resistor 64. A trimpot 82 and a feedback resistor 62 are coupled between the output and amplifier 60 and its inverting input. The values of resistors 62 and 64 and trimpot 82 are chosen in this embodiment to provide amplifier 60 with a variable gain of twenty-seven to thirty-seven.

A resistor 66 is coupled between the noninverting input of amplifier 60 and ground, and the arm of a balance adjustment potentiometer 65 is coupled to the noninverting input by a resistor 63. The potentiometer 65 is coupled between plus and minus-twelve volt supplies.

The output of integrator 50 is coupled to an identically configured amplifier 70 which includes an inverting input resistor 74, a feedback resistor 72, noninverting input resistors 73 and 76, and a balance adjustment potentiometer 75. Amplifier 70 likewise provides a gain of seventy-five for signals produced by the second integrator 50.

The output of amplifier 60 is coupled to the noninverting input of a comparator 80. The output of amplifier 70 is coupled to the inverting input of comparator 80, and to the inverting input of a comparator 90. A voltage divider including serially coupled resistors 92 and 94 is coupled between a −12 volt supply and ground. The junction of resistors 92 and 94 is coupled to the noninverting input of comparator 90.

The output of comparator 80 is coupled by a diode 86 to an input of an NAND gate 100. A load resistor 88 is coupled between the input of NAND gate 100 and ground. The output of comparator 90 is coupled by a diode 96 to a second input of NAND gate 100. A load resistor 98 is coupled between the second input of NAND gate 100 and ground. The output of NAND gate 100 is coupled to the "set" input S of an R-S type flip-flop 106. The "reset" input R of flip-flop 106 is coupled to one terminal of a toggle switch 116, the other terminal of which is coupled to the +12 volt supply by a resistor 118. A pull-down resistor 108 is coupled between the R input of flip-flop 106 and ground.

The output of flip-flop 106 is coupled by a resistor 102 and a diode 104 to the base of a transistor 110. The emitter of transistor 110 is coupled to ground, and its collector is coupled to a +24 volt supply by a relay coil 112. A protection diode 114 is coupled across the relay coil 112. When the relay coil is energized, a spring-loaded clamp 120 may be manually set so that blood is permitted to flow through a tubing segment 122. The tubing segment 122 is serially located downstream from the tubing or drip chamber located in the transceiver 20. When air is detected in the blood by the transceiver 20, the system is activated to de-energize the relay, thereby releasing the clamp which blocks tubing segment 122 and prevents the flow of air-contaminated blood to the patient.

In operation, when power is applied to the bubble detector of FIG. 1, the toggle switch 116 is closed to reset the flip-flop 106 and permit the relay coil 112 to hold the clamp 120 in its withdrawn position so that the tubing segment 122 is not closed. System operation will then proceed as long as the transducer 24 is receiving relatively strong signals from transducer 22 by way of the blood path. If for any reason the transducers are not operating properly, no signals will be produced by half-wave rectifier 30, and the system will go to a condition in which a −0.4 volt level will be developed at the inverting input of amplifier 90. The voltage divider 92, 94 will present a constant −0.6 volt level at the noninverting input of comparator 90 so that, under these conditions, a low signal level will be developed at the output of comparator 90. This low signal level will cause the output of NAND gate 100 to go to its high state, setting flip-flop 106 and triggering an alarm condition which will release the clamp 120 and block the blood flow.

When the bubble detector of FIG. 1 is operating under normal conditions and the blood flow between the transducers 22 and 24 is not contaminated with bubbles, the half-wave rectifier 30 is producing a sequence of negative-going pulses. These pulses are integrated by integrators 40 and 50 to produce relatively constant signal levels which are amplified by amplifiers 60 and 70. Under these conditions, amplifier 70 will produce a relatively constant −5 volt signal level at the inverting input of comparator 80. Amplifier 60 will produce a voltage level at the non-inverting input of comparator 80 which is less negative (approximately −4 volts) as regulated by the gain setting of trimpot 82. The negative voltage applied to comparator 90 by comparator 70 will produce a high signal level at one input of NAND gate 100. Comparator 80 will produce a high signal level at the other input of NAND gate 100, and the output of NAND gate 100 will be low. The signal levels at the input of comparator 80 are representatively shown in FIG. 2C, where $V_{50}$ is the voltage level at the inverting input of the comparator and $V_{40}$ is the less negative voltage level at the noninverting input of the comparator 80 by reason of the variable gain of amplifier 60. The two signal levels differ by an amount indicated by arrow 200.

The steady state levels of signals $V_{40}$ and $V_{50}$ in FIG. 2C will always be separated by the same proportional amount (arrow 200), regardless of the effective coupling of the transducers 22 and 24 with the intervening blood tubing or drip chamber. When the coupling is good, relatively large amplitude pulses will be produced by the half-wave rectifier 30 and relatively large negative signal levels will be developed at the inputs of comparator 80. When the coupling is poor, relatively low negative signal levels will be present at the inputs of the comparator 80. The levels will always be separated in the same proportion, however.

When bubbles begin to occur in the blood flow between the transducers 22 and 24, the pulses produced by the half-wave rectifier 30 will decrease in amplitude. These pulses are integrated by integrators 40 and 50, causing their output signal levels to decline. But due to the difference in time constant values, the output signal of integrator 50 will decline rapidly while the output of integrator 40, with its much slower time constant, will change imperceptibly at first. The rapid decline in the output signal of integrator 50 will result in a sharp decline towards ground of the $V_{50}$ signal at the inverting input of comparator 80. A continuation of this occurrence will soon cause the $V_{50}$ signal level to be less negative than the $V_{40}$ signal level, as shown in FIG. 2C. When the $V_{50}$ level falls below the level of $V_{40}$, the output of the comparator 80 will go to its low state, initiating an alarm condition which will block the blood flow in tubing segment 122. The alarm condition will end, permitting the clamp 120 to be reset, when the $V_{50}$ signal level produced by the fast (short time constant) integrator 50 again goes more negative than the reference signal level produced by the slow (long time constant) integrator 40 at the junction of voltage divider 82, 84.

FIGS. 2A and 2B illustrate the operation of prior art arrangements, in which the integrated transducer signal $V_T$ is compared with a fixed reference value $V_r$.

FIG. 2A depicts signal conditions which may occur when ultrasonic signal coupling through the drip chamber or blood tubing are good. Under these conditions, a relatively high signal level $V_T$ can develop, which far exceeds the reference level $V_r$ under normal conditions. The passage of bubbles past the transducers will cause a drop in this $V_T$ signal level toward the $V_r$ reference level, but the steady-state $V_T$ signal level may be so high that the signal does not reach the $V_r$ level, and the bubbles will pass undetected. On the other hand, when coupling through the blood path is poor, the steady-state level of the $V_T$ signal may be very close to the $V_r$ reference level, as shown in FIG. 2B. Under these conditions even a small drop in the $V_T$ signal level due to the passage of a few small, isolated bubbles may be enough to trigger the system alarm and block the blood flow. Such a condition can frequently interrupt a hemodialysis treatment with troublesome false alarms.

What is claimed is:

1. Apparatus for detecting the presence of a contaminant in a fluid which passes through a passageway comprising:
    means for directing energy toward said passageway, said energy being of a form which is affected by the presence or absence of said contaminants;
    means for receiving energy transmitted through said passageway and responsively producing a first signal representative of the amount of said contaminant contained in said fluid;
    means, responsive to said first signal, for producing a dynamic reference signal which varies relatively slowly as a function of the level of said first signal;
    means, responsive to said first signal, for producing an indication signal which varies relatively quickly as a function of the level of said first signal; and
    means, responsive to said dynamic reference signal and said indication signal, for producing a signal indicative of the presence of a contaminant in said fluid when said indication signal exceeds said dynamic reference signal.

2. The arrangement of claim 1, wherein said contaminant comprises air bubbles, and further comprising:
    means, responsive to the occurrence of said signal indicative of the presence of said contaminant, for stopping the passage of said fluid through said passageway.

3. The arrangement of claim 2, wherein said dynamic reference signal producing means comprises a first integrator which exhibits a relatively long time constant, and said indication signal producing means comprises a second integrator which exhibits a relatively short time constant.

4. The arrangement of claim 3, wherein said means for producing a signal indicative of the presence of contaminant includes a comparator for receiving and analyzing said dynamic reference signal and said indication signal.

5. The arrangement of claim 4, wherein said fluid comprises blood, said energy directing means comprises a first ultrasonic transducer, and said first signal producing means includes a second ultrasonic transducer.

6. The arrangement of claim 4, wherein said means for producing a signal indicative of the presence of a contaminant further includes a logic function gate having a first input coupled to the output of said comparator, a second input, and an output coupled to said means for stopping the passage of said fluid; and further comprising:
    means, having an input coupled to said indication signal producing means and an output coupled to said second input of said logic function gate, for producing a failure indication signal indicative of the absence of said first signal.

7. The arrangement of claim 6, wherein said failure indication signal producing means comprises a second comparator having a first input coupled to said second integrator, a second input coupled to a source of reference potential, and an output coupled to said second input of said logic function gate.

8. The arrangement of claim 2, further comprising:
    means, coupled to said first signal producing means, and responsive to the absence of said first signal for producing a failure indication signal
    wherein said means for stopping the passage of said fluid is further responsive to said failure indication signal.

* * * * *